US00PP21864P2

(12) United States Plant Patent
Bacon

(10) Patent No.: US PP21,864 P2
(45) Date of Patent: Apr. 12, 2011

(54) PLUM TREE NAMED 'SUPLUMFORTY'

(50) Latin Name: *Prunus salicina*
Varietal Denomination: Suplumforty

(75) Inventor: Terry Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 12/583,126

(22) Filed: Oct. 29, 2009

(51) Int. Cl.
*A01H 5/00* (2006.01)

(52) U.S. Cl. ..... Plt./184

(58) Field of Classification Search ..... Plt./184
See application file for complete search history.

(56) References Cited

U.S. PATENT DOCUMENTS

PP4,902 P 10/1982 Weinberger
PP13,395 P3 12/2002 Fear et al.

*Primary Examiner* — Susan B McCormick Ewoldt
(74) *Attorney, Agent, or Firm* — Knobbe, Martens, Olson & Bear, LLP

(57) ABSTRACT

A new and distinct plum tree variety, *Prunus salicina,* cv. 'Suplumforty' is characterized by ripening mid-season. The new variety is further characterized by dark skin and reddish flesh color.

1 Drawing Sheet

Latin name of the genus and species claimed: *Prunus salicina.*

Variety denomination: 'Suplumforty'.

BACKGROUND AND SUMMARY OF THE INVENTION

This invention relates to the discovery and asexual propagation of a new and distinct variety of plum, *Prunus salicina* cv. 'Suplumforty'. The new variety was first hybridized in 2002 and selected in July 2004 by Terry Bacon as breeder number: 'PL453RB'. The new variety was first evaluated by Terry Bacon near Wasco, Calif. in Kern County. The variety 'Suplumforty' was originated by hybridization.

The new variety 'Suplumforty' is characterized by ripening mid-season and having dark skin and reddish flesh color.

The seed parent is 'Suplumtwentyfour' (the subject of U.S. Plant Pat. No. 13,395), and the pollen parent is an unknown plum in the breeding population. The parent varieties were first crossed in March of 2002, with the date of planting of the progeny being January 2003, and the date of first flowering being March 2004. The new plum variety 'Suplumforty' was first asexually propagated by Terry Bacon near Wasco, Kern County, Calif. in January 2006, by grafting.

The new variety 'Suplumforty' is distinguished from its seed parent, 'Suplumtwentyfour', in that the new variety ripens about nineteen days later than 'Suplumtwentyfour'.

The new variety 'Suplumforty' has a similar harvest time as 'Suplumeleven' (U.S. Plant Pat. No. 4,902), but the skin is darker and the flesh is more red in color. The new variety 'Suplumforty' has a harvest time seven days after Black Amber (unpatented).

The new variety 'Suplumforty' has been shown to maintain its distinguishing characteristics through successive asexual propagations by, for example, budding and grafting.

BRIEF DESCRIPTION OF THE PHOTOGRAPH

The accompanying color photographic illustration shows typical specimens of the foliage and fruit of the present new plum variety 'Suplumforty'. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England.

The descriptive matter which follows pertains to 4 year old 'Suplumforty' plants on Nemared (unpatented) rootstock, grown in the vicinity of Wasco, Kern County, Calif., during July 2009, and is believed to apply to plants of the variety grown under similar conditions of soil and climate elsewhere.

TREE

General: (Measurements taken on 4 year old tree unless otherwise noted.)

*Size.*—Medium. Normal for most plum varieties. Reaches a height of approximately 3 meters including normal pruning.

*Spread.*—Normal for most plum varieties. Approximately 3 meters.

*Vigor.*—Moderately vigorous.

*Growth.*—Semi-upright.

*Productivity.*—Very productive. Fruit set is usually two or more times desired amount for marketable size fruit.

*Form.*—Vase formed.

*Bearer.*—Regular.

*Fertility.*—Unknown.
*Canopy density.*—Medium-dense.
*Hardiness.*—Half-hardy in all fruit growing areas of California.
*Disease resistance/susceptibility.*—No specific testing for relative plant disease resistance/susceptibility has been designed. Under close observation in Kern County, Calif., no particular plant/fruit disease resistance/susceptibility has been observed.

Trunk: (Measurements at approximately 30 cm above soil line.)
*Diameter.*—Approximately 21 cm, varies with soil type, fertility, climatic conditions and cultural practices.
*Texture.*—Medium shaggy, increases with age of tree.
*Trunk color.*—About Grey-green 198C to Grey-brown 201A; becomes darker with age.

Branches: (Measurements at approximately 90 cm above soil line.)
*Size.*—Diameter ranges from approximately 6 to approximately 9 cm.
*Texture.*—Smooth on first year wood, increasing roughness with tree age.
*Color.*—Branches vary from about Grey-brown 199B to Brown 200B.
*Number of lenticels.*—Medium, when present, about 2-3/cm$^2$.
*Lenticels density.*—Approximately 2-4 per cm$^2$.
*Lenticels color.*—About Grey-brown 199C.
*Lenticels size.*—Medium, about 2 mm.
*Lenticels length.*—Approximately 3 mm.
*Lenticels width.*—Approximately 1 mm.

Flowering shoots: (Data taken in July at midpoint of previous season shoots.)
*Size.*—Average diameter approximately 6 mm.
*Color.*—Topside: About Grey-brown 197B. Underside: About Grey-brown 197B.
*Internode length.*—Medium; approximately 25 mm. Midway on flowering shoot.
*Flowering shoot lenticels.*—Sparse. Color: About Grey-orange 164B. Diameter: Approximately 0.5 mm.
*Flowering shoot leaf buds.*—Shape: Obovate. Width: Approximately 0.8 mm. Length: Approximately 1 mm. Color: About Grey-orange 166C.
*Flowering shoot flower buds.*—Shape: Obovate-pointed, borne usually on short spurs, approximately 1-3 cm long. Width: Approximately 1.3 mm. Length: Approximately 2 mm. Color: About Grey-orange 166C. Number per Spur: Usually 20-30 on short spurs. Position: Free.
*Density of buds.*—Dense.
*Flower bud distribution.*—Generally 20-30 on short spurs.
*Ratio of wood (leaf) buds to flowering buds.*—1/20 on short spurs.

FOLIAGE

Leaves:
*Size.*—Medium.
*Average length.*—Medium; approximately 81 mm without petiole.
*Average width.*—Medium; approximately 36 mm.
*Thickness.*—Medium, about 0.3 mm.
*Color.*—Upper surface: About 147A. Lower surface: About 147B.
*Form.*—Elliptic.
*Tip.*—Acuminate.
*Base.*—V-shaped.
*Margin.*—Crenate.
*Venation.*—Pinately veined.
*Vein color.*—About 139D on lower surface.
*Surface texture.*—Smooth.
*Leaf blade (ratio of length to width).*—Medium.
*Shape in the cross section.*—Flat.
*Profile.*—Somewhat flat.
*Leaf blade tip.*—Usually in the plane of the leaf.
*Undulation of margin.*—Absent.

Petiole:
*Average length.*—Medium; approximately 18 mm.
*Average diameter.*—Approximately 2 mm.
*Color.*—About 147C.

Leaf glands:
*Form.*—Reniform, Very rare.
*Average number.*—Most leaves have none. Where they exist about two/leaf.
*Position.*—On leaf base.
*Average size.*—Small; approximately 0.5 mm.
*Color.*—About 200D.

FLOWERS

General:
*Flower blooming period.*—First bloom: Approximately February 26. Full bloom: Approximately March 1.
*Duration of bloom.*—Medium; approximately 10 days.
*Diameter of fully opened flower.*—Medium, approximately 25 mm.
*Flower aroma.*—Slight aroma.
*Shape.*—Rosaceous.

Peduncle:
*Length.*—Medium; approximately 10 mm.
*Diameter.*—Medium; approximately 1 mm.
*Color.*—About Yellow-green 144B.
*Pubescence.*—Absent.

Petals:
*Number.*—5.
*Arrangement.*—Free.
*Length.*—Approximately 10 mm.
*Diameter.*—Approximately 10 mm.
*Shape.*—Circular.
*Apex shape.*—Rounded.
*Base shape.*—Narrows at point of attachment.
*Color.*—About White 155D.
*Surface texture.*—Smooth.
*Margins.*—Slightly undulating.
*Claw length.*—Medium, approximately 2.0 mm.
*Margin waviness.*—Medium, smooth and slightly wavy.
*Base angle.*—Narrow.
*Division of upper margin.*—Entire.
*Pubescence of inner surface.*—Absent.
*Pubescence of outer surface.*—Absent.

Sepals:
*Number.*—5.
*Length.*—Approximately 3 mm.
*Diameter.*—Approximately 2 mm.
*Shape.*—Elliptic.
*Color.*—About Yellow-green 144A.
*Surface texture.*—Smooth.
*Margins.*—Entire.
*Positioning.*—Adpressed or touching petals.

*Pubsencence of inner surface.*—Absent.
*Pubescence of outer surface.*—Absent.

Stamens:
*Number.*—Ranges from approximately 20 to approximately 30.
*Average length.*—Approximately 7 mm.
*Filament color.*—About white 155D.
*Anther color.*—About Grey-orange 167A.
*Flower pollen color.*—About Grey-orange 167A.
*Position.*—Perigynous.

Pistil:
*Number.*—Usually one, occasionally two.
*Average length.*—Approximately 10 mm.
*Ovary diameter.*—Approximately 0.9 mm.
*Pubescence.*—None.
*Stigma extension in comparison to anthers.*—Usually below.
*Style pubescence* (*of base*).—Absent.

Receptacle:
*Depth.*—Medium.
*Pubescence of inner surface.*—Absent.
*Pubescence of outer surface.*—Absent.

FRUIT

General: (Description taken near Wasco, Kern County, Calif.)
*Harvest.*—
*Date of first pick.*—Approximately July 1.
*Date of last pick.*—Approximately July 15.

Maturity when described: Firm.
Season ripening: Mid-season.
Position of maximum diameter: Towards the middle.
Symmetry about the suture: Nearly symmetric.

Size:
*Length* (*stem end to apex*).—Approximately 66 mm.
*Diameter perpendicular to suture plane.*—Approximately 66 mm.
*Average weight.*—Approximately 150 gm.

Form:
*Viewed from apex.*—Rounded, nearly symmetrical.
*Viewed from side, facing suture.*—Rounded, nearly symmetrical.
*Viewed from side, perpendicular to suture.*—Rounded, nearly symmetrical.

Apex shape: Rounded.

Fruit stem cavity:
*Shape.*—Flaring, rounded.
*Depth.*—Approximately 0.5 cm.
*Breadth.*—Approximately 1 cm.
*Width.*—Medium, approximately 15 mm.

Fruit stem:
*Length.*—Approximately 9 mm.
*Diameter.*—Approximately 3 mm.
*Color.*—About 147D.

Fruit skin:
*Thickness.*—Medium, approximately 0.3 mm.
*Adherence to flesh.*—Medium.
*Surface texture.*—Smooth.
*Pubescence.*—None.
*Bloom.*—Medium, slight bloom.
*Ground color.*—About 144A, when visible.
*Overcolor.*—About 187A.
*Taste.*—Mildly tart.
*Reticulation.*—Absent.
*Roughness.*—Absent.
*Tendency to crack.*—None.

Flesh:
*Ripens.*—Evenly.
*Texture.*—Firm, juicy.
*Fibers.*—Few.
*Flavor.*—Sweet-mild.
*Brix.*—Approximately 16°.
*Juice.*—Abundant to moderate.
*Aroma.*—Noticeable when ripe.
*Color.*—About 61C.
*Acidity.*—Medium-low.
*Eating quality.*—Good.
*Stone/flesh ratio.*—1.9/34.
*Firmness.*—Medium.

Pit cavity size:
*Length* (*diameter in line with suture plane*).—Approximately 16 mm.
*Diameter perpendicular to suture plane.*—Approximately 12 mm.
*Color.*—About 63C.

Fruit use: Fresh market.

Fruit shipping and keeping quality: Good, holds well in cold storage and maintains good firmness and eating quality, minimal bruising and scarring in packing and shipping trials.

Suture line: Inconspicuous.

Stone: (Measurements taken on dried stones.)
*Stone freeness.*—Semi-free.
*Degree of adherence to flesh.*—Weak.
*Stone size.*—Size compared to Fruit: Small. Length (Diameter in line with suture plane): Approximately 16 mm. Diameter perpendicular to suture plane: Approximately 12 mm. Width of Stalk End: Medium; approximately 7 mm. Angle of Stalk end: Obtuse. Hilum: Broad.
*Stone form.*—Viewed from side: Somewhat oval, asymmetric. Viewed from ventral side: Somewhat oval. Viewed from stem end: Somewhat oval.
*Stone shape.*—Base shape: Nearly straight. Apex shape: Nearly rounded to slightly pointed.
*Stone surface.*—Furrowed and pitted throughout.
*Stone halves.*—Nearly symmetric.
*Stone ridges.*—Rounded irregularly throughout.
*Stone outgrowing keel.*—Partially developed.
*Stone tendency to split.*—Slight in wet season.
*Stone color.*—About 165C.
*Position of maximum.*—Toward middle.
*Ventrical edge.*—Medium thin with slight wing.
*Dorsal edge.*—Medium shallow grooves interrupted.

What is claimed is:

1. A new and distinct plum tree as herein described and illustrated.

* * * * *

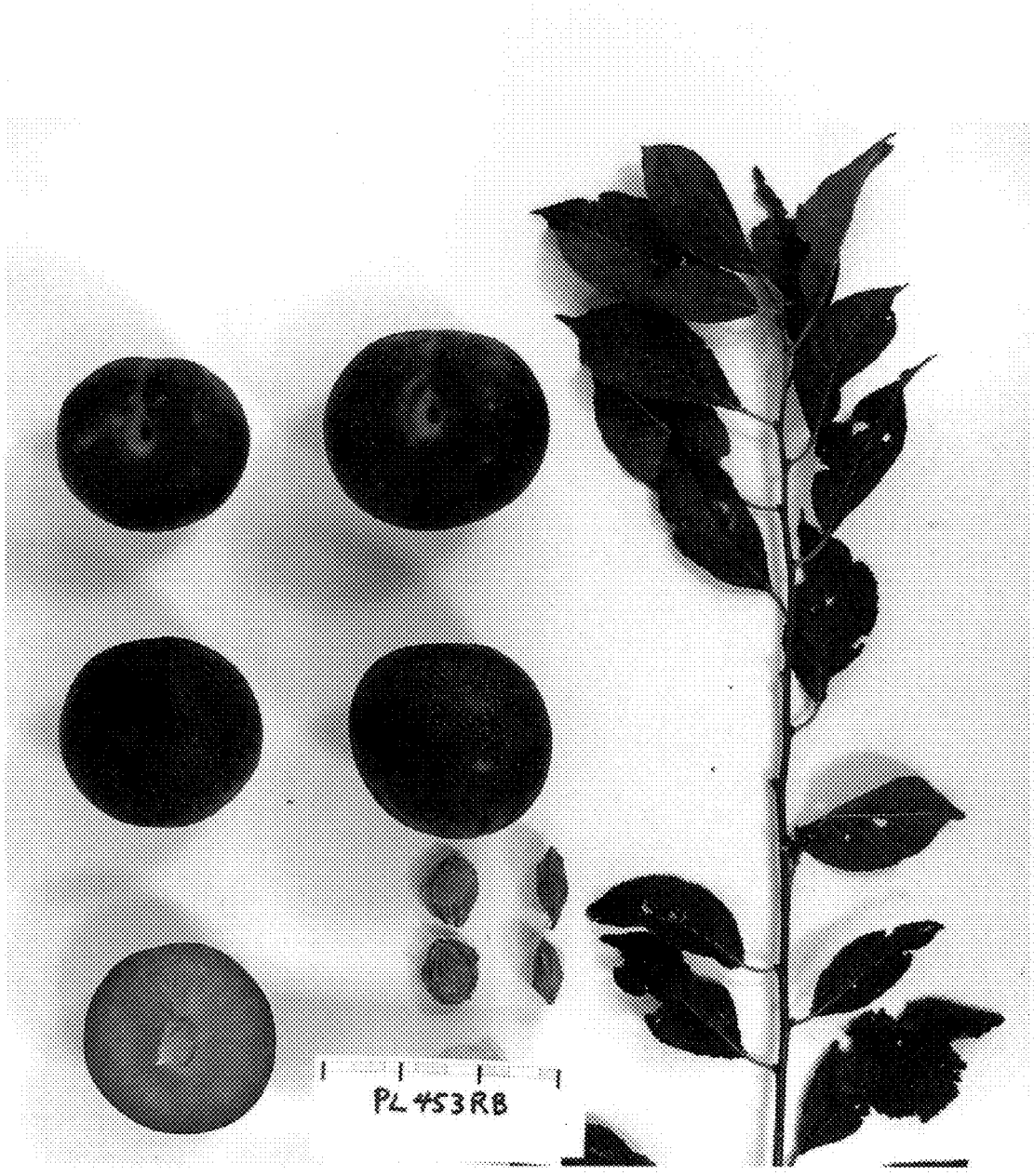
PL453RB